(12) United States Patent
Menne et al.

(10) Patent No.: US 6,736,784 B1
(45) Date of Patent: May 18, 2004

(54) MEDICAL INSTRUMENT FOR TREATING BIOLOGICAL TISSUE AND METHOD FOR TRANSMITTING PRESSURE WAVES

(75) Inventors: Andreas Menne, Meersburg (DE); Thomas Jerger, Sindelfingen (DE)

(73) Assignee: Ferton Holding S.A., Delemont (CH)

( * ) Notice: Subject to any disclaimer, the term of this patent is extended or adjusted under 35 U.S.C. 154(b) by 0 days.

(21) Appl. No.: 10/018,805
(22) PCT Filed: May 25, 2000
(86) PCT No.: PCT/EP00/04771
§ 371 (c)(1), (2), (4) Date: May 6, 2002
(87) PCT Pub. No.: WO01/00094
PCT Pub. Date: Jan. 4, 2001

(30) Foreign Application Priority Data

Jun. 24, 1999 (DE) .......................................... 199 29 112

(51) Int. Cl.[7] .............................. A61N 7/00; A61B 17/22
(52) U.S. Cl. ................................ 601/2; 601/4; 606/128
(58) Field of Search ........................ 601/2–4; 606/128; 367/147, 163, 174, 175

(56) References Cited

U.S. PATENT DOCUMENTS

| 3,970,076 A | * | 7/1976 | Hepp et al. ................. 601/21 |
| 4,603,701 A | * | 8/1986 | Chen ........................... 600/459 |
| 4,727,875 A | * | 3/1988 | Dory ............................. 601/4 |
| 5,273,027 A | * | 12/1993 | Sekino et al. ................. 601/54 |
| 5,494,038 A | * | 2/1996 | Wang et al. ................. 600/459 |
| 5,748,563 A | * | 5/1998 | Hofmann ................... 367/147 |
| 6,413,230 B1 | * | 7/2002 | Haupt et al. ................... 601/2 |

FOREIGN PATENT DOCUMENTS

| DE | 2351247 A1 | | 4/1975 | |
| DE | 19725477 A1 | * | 12/1998 | ......... A61B/17/225 |
| WO | WO 94/17771 | * | 8/1994 | ........... A61H/23/00 |
| WO | WO 96/25888 | * | 8/1996 | ........... A61B/17/22 |
| WO | WO 96/28213 | * | 9/1996 | ............. A61N/7/00 |
| WO | WO 98/07470 | * | 2/1998 | ............. A61N/7/00 |
| WO | WO 98/32379 | * | 7/1998 | ............. A61B/8/00 |
| WO | WO 01/00094 A1 | * | 1/2001 | ........... A61B/17/22 |

* cited by examiner

Primary Examiner—Shawna Jeannine Shaw
(74) Attorney, Agent, or Firm—Diller, Ramik & Wight

(57) ABSTRACT

A medical instrument for treating biological tissue comprises a housing (2), a pressure wave generation means (4) and a transmission means (8) for coupling the unfocused pressure waves into the body of living beings. The transmission means (8) comprises a pressure chamber (12) having an inlet and an outlet end, the pressure chamber (12) containing a liquid (14) into which pressure waves from the pressure wave generation means (4) can be coupled, which pressure waves can be transmitted to a membrane (16) arranged at the outlet end of the pressure chamber (12) which membrane (16) couples the pressure waves transmitted from the liquid unfocusedly into the biological tissue.

12 Claims, 3 Drawing Sheets

MEDICAL INSTRUMENT FOR TREATING BIOLOGICAL TISSUE AND METHOD FOR TRANSMITTING PRESSURE WAVES

BACKGROUND OF THE INVENTION

The invention relates to a medical instrument for treating biological tissue.

Such instruments serve for accelerating or starting the healing process in the case of bone fractures, bone injuries, but also periodontosis by means of pressure or shock waves. Another application is the pain therapy in the case of tendopathies.

In the extracorporeal pressure wave instruments known so far a pulsed pressure or shock wave is generated in the focus of an acoustical reflector, e.g. by means of spark discharge, as described in the German laid open patent application DE 23 51 247 A, the wave being focused via the reflector onto the object to be treated with the waves. It is assumed that the pressure waves produce microlesions in the biological tissue, which induce the body to take regeneration measures.

Known pressure wave instruments have a narrow localized focal area in which only a therapeutical effect is observed. The reason for this is that these pressure wave instruments, so-called extracorporeal lithotriptors, have been developed for crushing body stones. During this application the overall energy is focused in a small area, in this case onto the body stone to be crushed. A satisfactory result of treatment of bone fractures and of pain therapy requires however a larger area to be uniformly treated with waves. This necessitates a complex motion mechanism and is very time-consuming due to the repeated search for the treatment position.

Another drawback of the extracorporeal pressure wave sources is that the focal area is invisible for the user. The focus lies outside the instrument proper. For a treatment the doctor therefore needs a localization system (ultrasonic and/or X-ray system) to bring focus and treatment location to coincidence.

In the German laid open patent application DE 197 25 477 A1 an instrument is described where a transmission element couples unfocused mechanically generated pressure waves into biological tissue. For this purpose the user must direct the blunt transmission element onto the treatment location. However, when this instrument, which is of very simple configuration, is used, motion of the transmission element, even if it is limited to a longitudinal deformation due to the influence exerted by a pressure wave, cannot be prevented. For applications where such an instrument is placed onto the skin surface the effect caused by the excursion of the transmission element, such as reddening and slight swelling, may be acceptable. However, for treatment of periodontosis such an instrument must be placed on the gums which does not withstand such a stress.

SUMMARY OF THE INVENTION

It is therefore the object of the invention to configure a medical instrument and a method for transmitting pressure waves such that uniform distribution of the pressure wave energy to a large spectrum is allowed in a simple and inexpensive way without the biological tissue being damaged during transmission of the pressure wave by means of the instrument onto the biological tissue.

The invention provides in an advantageous manner that the transmission means comprises a liquid-filled pressure chamber, the liquid contained therein transmitting coupled-in pressure waves to a membrane arranged at the outlet end of the pressure chamber, the membrane unfocusedly coupling the pressure waves transmitted by the liquid into the biological tissue.

Since the impedance of the liquid corresponds to a large degree to the impedance of the biological tissue into which the pressure wave is to be coupled, no transmission losses occur during the transmission of the pressure wave from the liquid via the membrane onto the biological tissue. In particular a uniform distribution of the pressure wave energy onto a large spectrum is possible without the biological tissue being damaged during transmission of the pressure wave.

A thin membrane is used as coupling means. On the one hand this membrane closes the pressure chamber at its outlet end and on the other hand does not impede coupling of the pressure waves from the liquid into the biological tissue. Further, the entry surface of the biological tissue is not mechanically stressed when the pressure wave is forwarded through the membrane such that the instrument can be applied to all types of biological tissue. Impedance-matched plastic films can be used as membrane.

The pressure chamber is preferably configured as an elongate duct. The duct form presents the advantage that the pressure wave coupled in by the pressure wave generation device cannot migrate sidewards and can in this way be transported as a plane wave over a longer distance without occurrence of any larger losses. Further, steepening of the pressure wave occurs in this preferably tubular duct due to the running length and the non-linear propagation properties such that the elongate duct operates like a shock wave tube. Due to the steepening of the pressure wave the physical variables of the pressure wave change within a shorter period of time and the crushing qualities of the pressure wave increase—an effect which is of advantage for producing microlesions.

The ratio of the pressure chamber length to the pressure chamber diameter preferably ranges between 2 and 10.

The pressure wave generation means may be arranged inside the pressure chamber. The pressure wave generation means generates an undirected pressure wave which propagates in a globular manner and whose energy thus rapidly decreases with the distance from its point of origin. If the locations of generation and application are not near each other, only a small portion of the energy used reaches its point of destination. To limit these losses, the liquid-filled pressure chamber may be configured such that the pressure wave generation means is arranged inside the tubular duct near its inlet end.

Alternatively it may be provided that the pressure wave generation means is located adjacent to the pressure chamber. In this case the exit interface of the pressure wave generation means is identical with the entry interface.

The pressure wave generation means can generate pressure waves in a piezoelectrical, magnetostrictive, electrostrictive, magnetic, electrical or mechanical manner.

The pressure wave generation means may e. g. comprise an electrohydraulic probe arranged in the pressure chamber, the probe generating a pressure wave by spark-over.

Alternatively, the pressure wave generation means may comprise a piezoelectric element arranged on the inlet end of the duct of the pressure chamber and directly adjacent to the liquid.

Further, the pressure wave generation means may comprise an electromagnetically excited membrane arranged on the inlet end of the pressure chamber and directly adjacent to the liquid.

In a preferred embodiment it is provided that the pressure wave generation means couples the pressure waves mechanically into the pressure chamber, and that an exit interface of a linearly guided transmission element, which is elastically supported in axial direction, is coupled to the liquid in the pressure chamber and transmits mechanically induced pressure waves to the liquid.

Alternatively, an internal membrane, which is elastically supported in axial direction, may be arranged at the inlet end of the pressure chamber, the membrane mechanically transmitting the coupled-in pressure waves to the liquid.

The transmission element or the internal membrane is energized by a linearly reciprocating beater part which, as a result of the impulse, mechanically induces a pressure wave which propagates up to the exit interface of the membrane or the transmission element.

The beater part is guided coaxially to the transmission element.

The pressure wave generation means periodically generates the coupled-in pressure waves. A larger number of successive individual pulsed pressure waves of weaker energy leads to a better healing success in the biological tissue than one individual strong pressure pulse. The pressure wave generation means can thus operate at a frequency of recurrence of individual pressure pulses of between 1 and 20 Hz, wherein approximately 1000 to 2000 pressure pulses are required for treating the biological tissue.

In the case of mechanical operation of the pressure wave generation means the driving means for continuous operation are preferably configured such that periodical motion of the drive unit is possible. If e. g. a pneumatic beater part is used which generates a pressure wave in a transmission element by its striking on said transmission element, the air flows may be such that the beater part performs a continuous reciprocal motion and periodically hits the transmission element.

Electrically operated pressure wave generation means are normally supplied by a capacitor battery. In the case of periodical operation the power supply for charging the batteries must be sufficiently high such that the given number of pressure pulses can be supplied at the required frequency of recurrence.

In further embodiments of the invention it is provided that the cross-section of the duct is flared or tapered towards the external membrane. A pressure chamber tapering towards the membrane intensifies the pressure wave by reduction of its cross-section. Flaring of the pressure chamber weakens the pressure wave but exposes a larger treatment surface to waves.

Between the external membrane and the biological tissue an impedance-matched medium may be provided which improves coupling of the pressure waves into the biological tissue. If the membrane does not rest absolutely flatly and without any air inclusions on the biological tissue, a portion of the pressure pulse is reflected on this acoustic discontinuity and the portion of pressure waves that can be coupled in is reduced. A suitable pasty impedance matching medium is e. g. an ultrasonic gel or any other pasty substances having a similar impedance as the biological tissue, e. g. vaseline.

BRIEF DESCRIPTION OF THE DRAWINGS

Hereunder embodiments of the invention are explained in detail with reference to the drawings in which.

DESCRIPTION OF THE PREFERRED EMBODIMENTS

Figure 1:
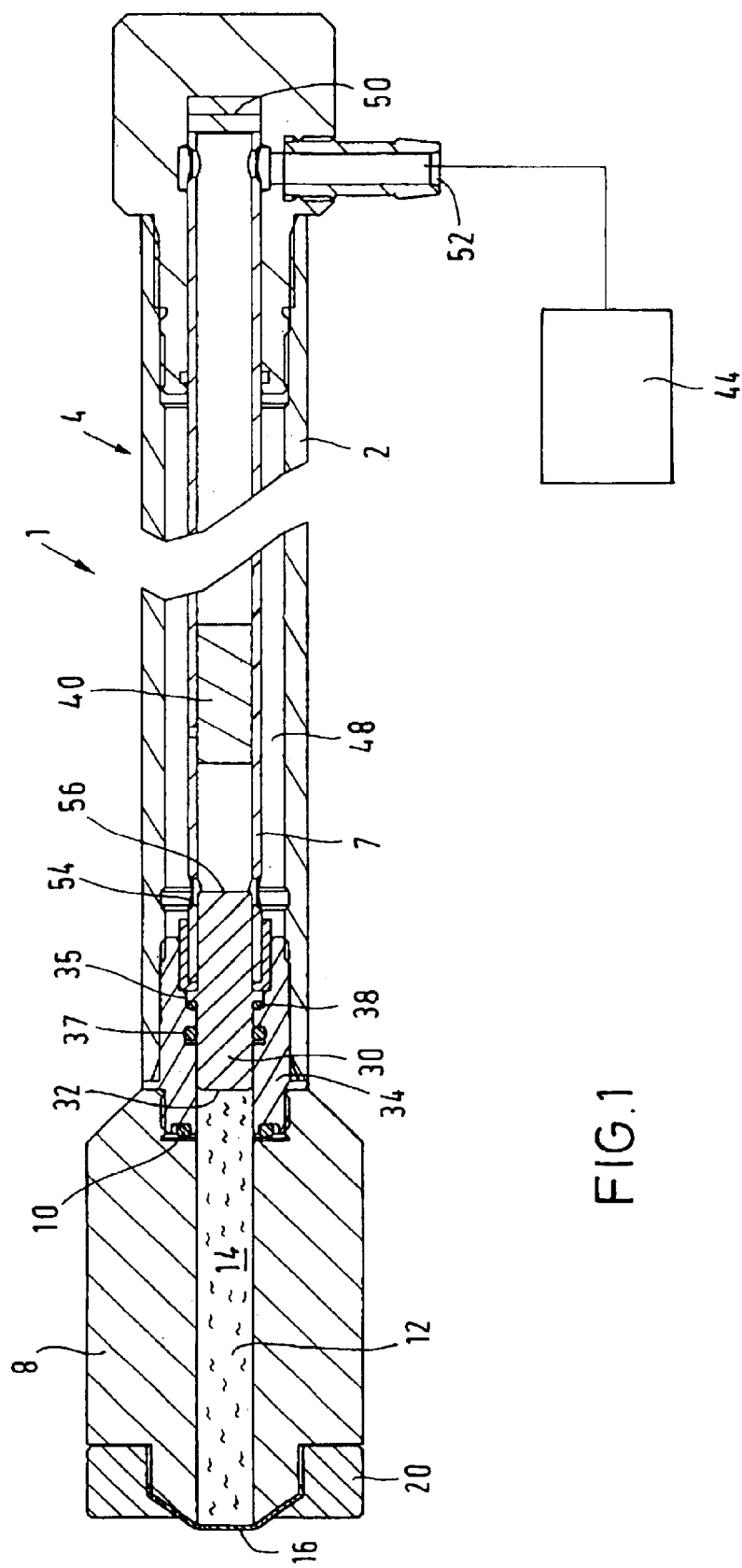
FIG. 1 shows a first embodiment with a mechanical pressure wave generation means.

The handpiece 1 shown in FIG. 1 comprises a housing 2 of a mechanical pressure wave generation means 4 having an inner cylinder 7, in which a beater part 40 is reciprocated between two end positions with the aid of pneumatic driving means 44 in connection with an impact pressure chamber 48 which coaxially and annularly surrounds the inner cylinder 7. At the distal end of the housing 2 a transmission means 8 for pressure waves is screw-mounted.

Alternatively it is also possible to move the beater part 40 hydraulically, mechanically, electromagnetically or by any other driving means. The length of the acceleration path can be selected in dependence on the mode of operation. In the case of a pneumatically operated beater part 40 and a pneumatic pressure of approximately 0.3 MPa (3 bar) the length of the acceleration path is approximately 50 to 200 mm. In the proximal end position of the beater part 40 at the end of the inner cylinder 7 a magnetic holder 50 is arranged which can retain the metallic beater part 40 in its proximal end position until a pneumatic pressure applied via the connection 52 accelerates the beater part 40 towards the distal end of the inner cylinder 7. The air upstream of the beater part 40 as seen in the direction of motion of the beater part 40 is led into the impact pressure chamber 48 via the annular slots 54 provided at the distal end of the inner cylinder 7. Due to the acceleration of the beater part 40 the latter hits at a high end velocity of e. g. 10–25 m/s onto an entry interface 56 of a transmission element 30 arranged at a distal end of the inner cylinder 7. The transmission element 30 comprises an essentially cylindrical metallic probe having an exit interface 32 of plane or slightly convex or concave configuration. The transmission element 30 is sildingly guided in a hollow-cylindrical receiving part 34. An annular collar 35 on the transmission element 30 serves as a stop for the receiving part 34, wherein between annular collar 35 and receiving part 34 a spring/damping element 38 is arranged which decouples the transmission element 30 from the receiving part 34 and ensures that the transmission element 30 returns, after the hitting process, into its initial position at the distal end of the inner cylinder 7. An O-ring 37 slidingly receiving the transmission element 30 seals the pressure wave generation means 4 against the transmission means 8 for the pressure waves.

The exit interface 32 of the transmission element 30 is in direct contact with a liquid-filled pressure chamber 12 of the transmission means 8. Preferably a substance having similar acoustical properties as biological tissue, e. g. water, serves as the liquid. The pressure chamber 12 can have an elongate cylindrical shape to steepen the pressure wave, but can also be of very short configuration when the pressure wave generation means 4 generates pressure waves of adequate intensity. The pressure chamber 12 is closed by a membrane 16 at the distal end. A tensioning device 20 tensions the membrane 16 over the distal end of the pressure chamber 12 and seals its outlet end against the surroundings such that the liquid 14 cannot leave the pressure chamber 3.

If the beater part 40 hits upon the entry interface 56 of the transmission element 30, a pressure wave is generated in the transmission element 30, which propagates up to the exit interface 32 of the transmission element 30 and is then coupled into the liquid 14 in the pressure chamber 12. The pressure wave travels in the pressure chamber 12 towards the distal membrane 16, steepens due to the non-linear wave propagation conditions and travels through the membrane 16 into the biological tissue which is in contact with the membrane 16.

After termination of the hitting process the spring/damping element 38 moves the transmission element 30 back into its initial position. The beater part 40 is returned by the overpressure in the impact pressure chamber 48 and the return flow of the air from the impact pressure chamber 48 through the annular slots 54 into its rest position at the proximal end of the inner cylinder 7 and retained by the magnetic holder 50. The instrument is now ready for another hitting process.

Figure 2:
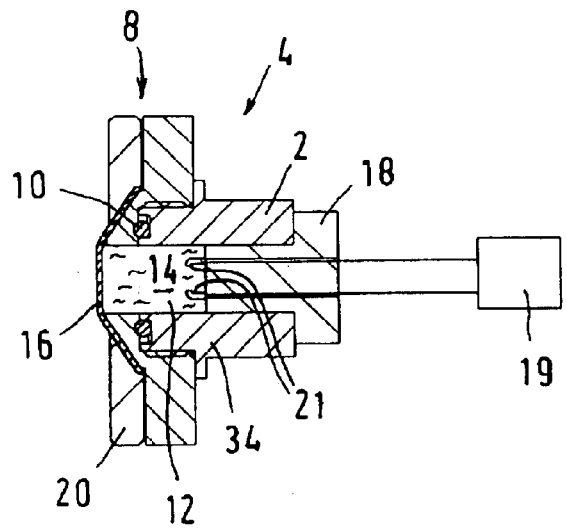
FIG. 2 shows a second embodiment with an electrohydraulic probe as pressure wave generation means.

FIG. 2 shows an embodiment with a spark discharge distance for generating pressure waves. An electrical circuit 19 supplies the two electrodes 21 of an electrohydraulic probe 18 with a short voltage pulse. If the surrounding liquid 14 in the pressure chamber 12 is electrically conducting, a spark-over occurs between the electrodes 21. Due to the resultant sudden plasma formation a pressure wave occurs which propagates in the pressure chamber 12 and is coupled via the membrane 16 into the biological tissue which is in contact with the membrane 16.

Figure 3:
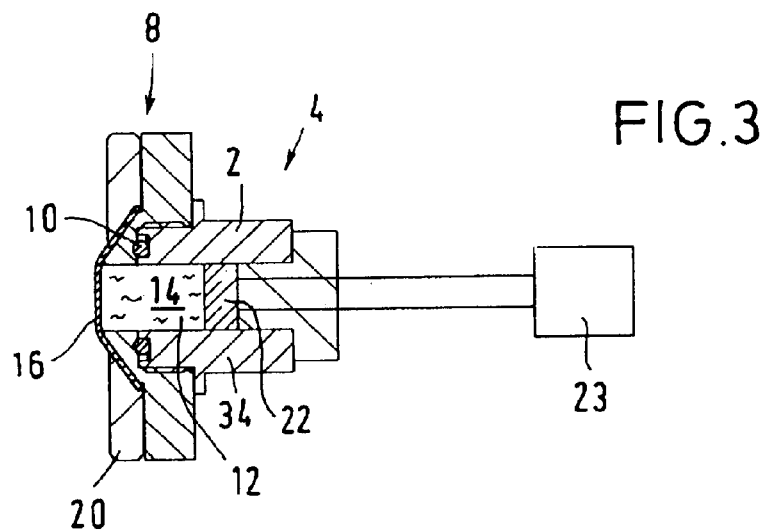
FIG. 3 shows a third embodiment with a piezoelectrical pressure wave generation means.

An alternative pressure wave generation means 3 is shown in FIG. 3. An electrical circuit 23 supplies a voltage pulse to a piezoelectrical element 22 arranged in the pressure chamber 12. The voltage pulse induces the piezoelectrical element 22 to expand and generates a pressure wave in the surrounding liquid 14.

Figure 4:
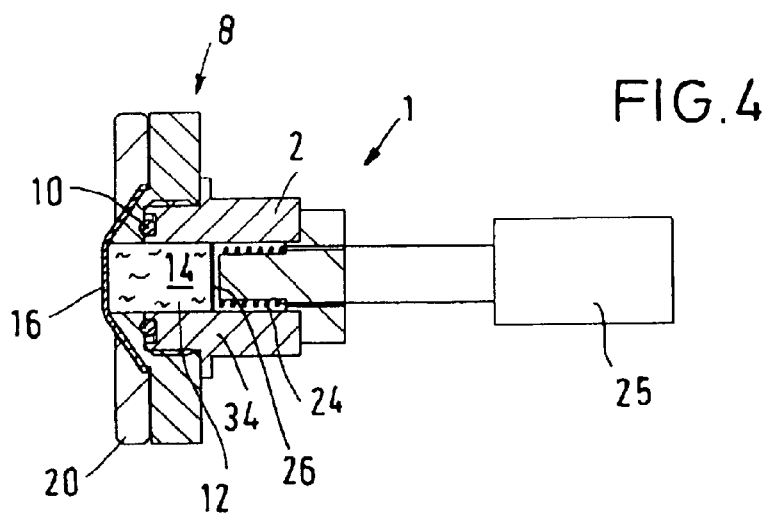
FIG. 4 shows a third embodiment with an electromagnetic pressure wave generation means.

FIG. 4 shows another alternative pressure wave generation means 4 comprising a coil arrangement 24 supplied with power by an electrical circuit 25. At the distal end of the coil arrangement 24 an exciting membrane 26 is arranged. The coil arrangement 24 induces an eddy current in the exciting membrane 26, which eddy current builds up a magnetic field. Due to the repellent forces between the coil arrangement 24 and the exciting membrane 26 the latter is jerkily moved away from the electrical coil arrangement 24 by a short power pulse from the electrical circuit 25, whereby a pressure wave is coupled into the pressure chamber 12.

Figure 5:
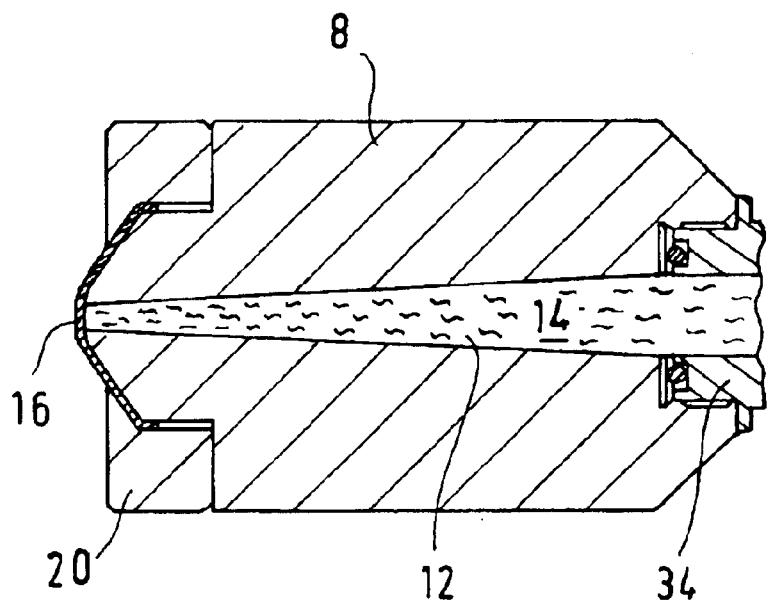
FIG. 5 shows a transmission means having a tapered pressure chamber.
Figure 6:
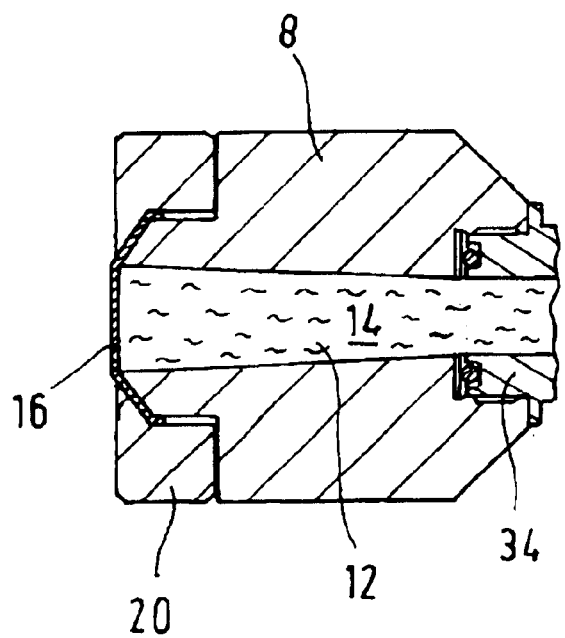
FIG. 6 shows a transmission means having a flared pressure chamber.

The transmission means 8 of the various embodiments differ from each other by the length and the shape of the pressure chamber 12. FIG. 5 shows a transmission means 8 where the pressure chamber 12 tapers in distal direction. A pressure wave generated by a pressure wave generation means 4 is intensified due to the reduction of the effective cross-section of the pressure chamber 12. If the pressure chamber 12 is of flared configuration, as shown in FIG. 6, the pressure wave is weakened but exposes a larger area to waves. If steepening of the pressure wave is not necessary or not desired, the pressure chamber 12 can be of short configuration, as in the embodiments shown in FIGS. 2 to 4.

The transmission means 8 is configured as a screw head and can be screw-mounted onto the pressure wave generation means 4. A seal 10 seals the transmission means 8 against the receiving part 34 of the pressure wave generation means 4. The pressure chamber 12 can extend up to and into the receiving part 34.

Although a preferred embodiment of the invention has been specifically illustrated and described herein, it is to be understood that minor variations may be made in the apparatus without departing from the spirit and scope of the invention, as defined by the appended claims.

What is claimed is:

1. A medical instrument for treating biological tissue, the instrument comprising a housing (2), a pressure wave generation means (4) and a transmission means (8) for coupling the unfocused pressure waves into the body of living beings, wherein the transmission means (8) comprises a pressure chamber (12) having an inlet end and an outlet end, the pressure chamber (12) containing a liquid (14) into which the pressure waves from the pressure wave generation means (4) can be coupled, which pressure waves can be transmitted from the outlet end of the pressure chamber (12) to the biological tissue, wherein the pressure waves transmitted by the liquid can be unfocusedly coupled into the biological tissue, characterized in that at the outlet end of the pressure chamber (12) a membrane (16) is arranged, the pressure chamber (12) comprises a duct in which a transmission element (30) linearly guided in axial direction is elastically supported, the transmission element (30) is coupled at an exit interface (32) to the liquid (14) in the pressure chamber (12), and the transmission element (30) is energized by a linearly reciprocating beater part (40) which, as a result of the impulse, mechanically induces a pressure wave.

2. The instrument as defined in claim 1 wherein the L/d-ratio of the duct-shaped pressure chamber (12) ranges between 2 and 10.

3. The instrument as defined in claim 1 wherein the beater part (40) is guided coaxially to the transmission element (30).

4. The instrument as defined in claim 2 wherein the beater part (40) is guided coaxially to the transmission element (30).

5. The instrument as defined in claim 1 wherein the pressure wave generation means (4) periodically generates the pressure waves.

6. The instrument as defined in claim 1 wherein the cross-section of the pressure chamber (12) is flared in distal direction towards the outer membrane (16).

7. The instrument as defined in claim 1 wherein the cross-section of the pressure chamber (12) tapers in distal direction towards the outer membrane (16).

8. The instrument as defined in claim 1 wherein the outer membrane (16) is exchangeably fastened to the transmission means (8).

9. The instrument as defined in claim 1 wherein a tensioning means (20) keeps the outer membrane (16) under pretension.

10. The instrument as defined in claim 1 wherein the outer membrane (16) comprises a fluid-tight and impedance-matched plastic film.

11. The instrument as defined in claim 1 wherein the liquid (14) contained in the pressure chamber (12) is saliferous.

12. The instrument as defined in claim 1 wherein between the outer membrane (16) and the biological tissue there is arranged an impedance-matched medium which improves coupling of the pressure waves into the biological tissue.

* * * * *